United States Patent
Wood

(10) Patent No.: US 8,869,796 B2
(45) Date of Patent: Oct. 28, 2014

(54) FILTER

(75) Inventor: Ian Wood, Warrington (GB)

(73) Assignee: Air Safety Limited, Warrington, Cheshir (GB)

( * ) Notice: Subject to any disclaimer, the term of this patent is extended or adjusted under 35 U.S.C. 154(b) by 1012 days.

(21) Appl. No.: 12/445,947

(22) PCT Filed: Oct. 17, 2007

(86) PCT No.: PCT/GB2007/003948
§ 371 (c)(1),
(2), (4) Date: Apr. 17, 2009

(87) PCT Pub. No.: WO2008/047108
PCT Pub. Date: Apr. 24, 2008

(65) Prior Publication Data
US 2010/0319699 A1 Dec. 23, 2010

(30) Foreign Application Priority Data
Oct. 17, 2006 (GB) .................................. 0620535.5

(51) Int. Cl.
| A62B 7/10 | (2006.01) |
| A62B 23/02 | (2006.01) |
| A62B 19/00 | (2006.01) |
| B03C 3/00 | (2006.01) |
| B01D 53/02 | (2006.01) |
| A61M 16/10 | (2006.01) |
| B03C 3/49 | (2006.01) |
| B03C 3/155 | (2006.01) |

(52) U.S. Cl.
CPC .............. B03C 3/155 (2013.01); A61M 16/105 (2013.01); A61M 2205/0233 (2013.01); A61M 16/1065 (2013.01); B03C 3/49 (2013.01)
USPC ...................... 128/205.29; 128/205.12; 96/58; 96/134

(58) Field of Classification Search
USPC .......................... 128/205.12, 201.25–201.28, 128/205.27–205.29; 96/74, 58, 134; 55/482, 498, DIG. 39
See application file for complete search history.

(56) References Cited

U.S. PATENT DOCUMENTS 2,195,565 A * 4/1940 Fricke .............................. 96/132
3,109,724 A * 11/1963 Heckman et al. ............... 55/514
(Continued)

FOREIGN PATENT DOCUMENTS

| EP | 0653219 | 5/1995 |
| FR | 2 879 942 | 6/2006 |

(Continued)

OTHER PUBLICATIONS

International Search Report from PCT/GB2007/003948, Feb. 27, 2008.

(Continued)

*Primary Examiner* — Melanie Hand
*Assistant Examiner* — Ned T Heffner
(74) *Attorney, Agent, or Firm* — Woodard, Emhardt, Moriarty, McNett & Henry LLP

(57) ABSTRACT

An air filter (1) particularly for use in a ventilator device for assisting respiratory function comprises: (i) a housing (3) with an air inlet (4) and an air outlet (6), and (ii) a filter material (8) in the path of air flow from the inlet (4) to the outlet (6). The filter material (8) is formed as a tubular body located at one of its ends around the air outlet (6) and being blanked (13) at its end opposite the air outlet (6). The air filter (1) further incorporates an electrostatically charged material (10) positioned at the blanked end (13) of the tubular body (8) to treat inlet air to the housing (3). This improves the life of the filter.

12 Claims, 1 Drawing Sheet

(56) References Cited

U.S. PATENT DOCUMENTS

| | | | |
|---|---|---|---|
| 3,556,097 A * | 1/1971 | Wallace | 128/202.23 |
| 3,615,233 A * | 10/1971 | Doering et al. | 422/117 |
| 4,063,913 A * | 12/1977 | Kippel et al. | 96/416 |
| 4,133,656 A * | 1/1979 | Kippel et al. | 96/416 |
| 4,171,962 A * | 10/1979 | Kippel et al. | 96/416 |
| 4,172,709 A * | 10/1979 | Kippel et al. | 96/416 |
| 4,386,948 A * | 6/1983 | Choksi et al. | 55/499 |
| 4,493,717 A * | 1/1985 | Berger et al. | 55/330 |
| 4,696,687 A * | 9/1987 | Billiet et al. | 96/136 |
| 4,826,515 A * | 5/1989 | Dyson | 55/345 |
| 4,853,011 A * | 8/1989 | Dyson | 55/345 |
| 5,160,356 A * | 11/1992 | Dyson | 55/345 |
| 5,186,165 A * | 2/1993 | Swann | 128/201.28 |
| 5,195,527 A * | 3/1993 | Hicks | 128/205.12 |
| 5,288,469 A * | 2/1994 | Skalla | 422/171 |
| 5,315,987 A * | 5/1994 | Swann | 128/201.28 |
| 5,394,867 A * | 3/1995 | Swann | 128/201.25 |
| 5,460,172 A * | 10/1995 | Eckerbom et al. | 128/201.13 |
| 5,478,377 A * | 12/1995 | Scavnicky et al. | 96/17 |
| 5,482,031 A * | 1/1996 | Lambert | 128/203.12 |
| 5,800,587 A * | 9/1998 | Kahlbaugh et al. | 55/486 |
| 5,996,580 A * | 12/1999 | Swann | 128/206.17 |
| 6,041,778 A * | 3/2000 | Swann et al. | 128/201.25 |
| 6,209,541 B1 * | 4/2001 | Wallace | 128/205.27 |
| 6,540,806 B2 * | 4/2003 | Reinhold | 55/490 |
| 6,758,212 B2 * | 7/2004 | Swann | 128/201.25 |
| 6,761,162 B1 * | 7/2004 | Swann | 128/201.25 |
| 6,854,460 B1 * | 2/2005 | Shofner et al. | 128/203.15 |
| 7,510,599 B2 * | 3/2009 | Brothier et al. | 96/29 |
| 2004/0025880 A1 * | 2/2004 | Capon et al. | 128/206.15 |
| 2004/0118397 A1 * | 6/2004 | Swann | 128/201.25 |
| 2005/0160911 A1 * | 7/2005 | Friday et al. | 96/134 |
| 2005/0160991 A1 * | 7/2005 | Miyamoto et al. | 118/728 |
| 2005/0247316 A1 * | 11/2005 | Orr | 128/205.12 |
| 2010/0319699 A1 * | 12/2010 | Wood | 128/205.12 |

FOREIGN PATENT DOCUMENTS

| | | |
|---|---|---|
| GB | 2267840 | 12/1993 |
| WO | WO 94/06482 | 3/1994 |
| WO | WO 99/44664 | 9/1999 |
| WO | WO 99/55422 | 11/1999 |
| WO | WO 02/066105 | 8/2002 |

OTHER PUBLICATIONS

Search report from GB0620535.5.

* cited by examiner

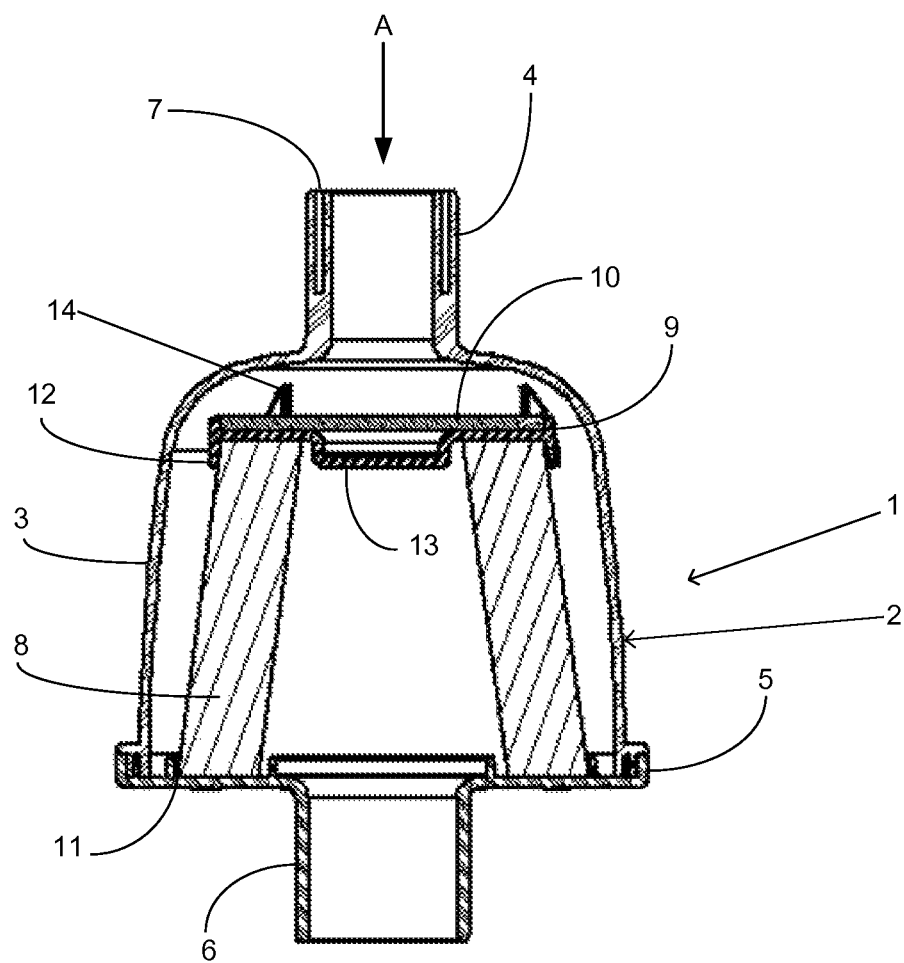

FILTER

CROSS REFERENCE TO RELATED APPLICATION

This application is a national stage of PCT/GB2007/003948 filed Oct. 17, 2007, which claims priority from GB 0620535.5 filed on Oct. 17, 2006.

The present invention relates to a filter intended particularly (but not necessarily exclusively) for use in a ventilator device for assisting respiratory function.

It is common practice for a patient on a ventilator in intensive care to receive nebulised drug therapy such as bronchial dilators and antibiotics to assist respiratory function. The patient will be connected to a ventilator through a breathing circuit and the drug will be administrated to them as a controlled and measured dosage. Exhaled air is then passed via the breathing circuit to the ventilator.

The exhaled air will entrain a quantity of the drug. It is important that this excess drug is removed from the airflow before it reaches the ventilator otherwise the flow transducers within the unit could become affected. An in-line filter is therefore provided in the breathing circuit for removing the drug. A filter is also essential to prevent the contamination of the local environment and to protect the staff from any adverse effects of the nebulised drugs.

Unfortunately, the filter will become blocked with the drug and other waste material during the course of this medical procedure. In turn, this will affect directly the performance and life of the filter. The filter must therefore be changed at regular intervals and before the build-up of waste material in the filter becomes too high to inhibit the airflow. The current practice is to change the filters when the pressure loss reaches 5 millibars (ideally 4.5 mbar). On current filter designs this point can be reached within 24-48 hours.

Clearly replacement of the filter involves the cost of its replacement. Additionally to install the replacement filter it is necessary for the breathing circuit of the ventilator to be "broken" and this can result in release of drugs into the local environment with risk of exposure to medical staff.

It is clearly desirable to provide a filter which requires replacement less frequently than conventional units.

According to the present invention there is provided an air filter comprising;

(i) a housing with an air inlet and an air outlet, and (ii) a filter material in the path of air flow from the inlet to the outlet, wherein the air filter further incorporates an electrostatically charged material positioned to treat inlet air to the housing.

We have found that the provision of an electrostatically charged medium within the air filter to treat incoming air serves to improve the life of the filter material. More particularly, the electrostatic medium is capable of attracting (and retaining) both liquid and particles so as to prevent their further travel into the filtration medium. Furthermore, the electrostatically charged medium may be absorbent and therefore retain moisture.

Preferably the electrostatically charged medium is of larger cross-sectional size than the air inlet.

The electrostatically charged medium may be in the form of a pad. The pad may be generally flat and positioned so as to be perpendicular to the path of air flow through the inlet. The electrostatic medium may, for example, be a fibrous material. In particular, the electrostatic medium may be a needled synthetic material inbued with an electrical charge during the course of manufacture. For example, the medium may be produced from a combination of two different fibres (e.g. a 50/50 combination) which are then needled at high speed (e.g. using about 1500 needles per sq inch) to impart a substantial electrostatic force.

The filter material may be pleated, e.g. a pleated paper. Such a paper may comprise glass fibre. The filter material may be a HEPA filter.

In a preferred construction of the invention, the filter material is in the form of a tubular body and is located at one of its ends around the air outlet. At its opposite end, the tubular body is "blanked-off" and the electrostatic medium is provided at the blanked end (external of the body). Preferably also in this embodiment the air inlet, the air outlet and the tubular body are all coaxial. This embodiment has the advantage that the electrostatic material (which may be in the form of a pad) causes the incoming air to diffuse, slow down and be diverted between the interior of the housing and the exterior periphery of the tubular body so that the air may then pass through the filter material.

The invention will now be further described, by way of example only, with reference to the accompanying drawings, in which:

FIG. 1 is a cross-sectional view of one embodiment of air filter in accordance with the invention.

The filter 1 illustrated in FIG. 1 comprises a two-part housing 2 formed of a cup-shaped body 3 having an air inlet 4 and a closure arrangement (or "lid") 5 having an air outlet 6. Cup-shaped body 3 and closure arrangement 5 are such that the air inlet 4 and the air outlet 6 are coaxial. Air inlet 4 is formed with an annular slot 7 for use in mounting the air filter 1 in a ventilation circuit.

Provided within the housing 2 is a tubular frustoconical body 8, formed of a filter material, an end cap 9 and a pad 10 of an electrostatic filter medium seated on end cap 9. More specifically, the lower (as viewed in FIG. 1) end of body 8 locates around the air outlet 6 and is encircled by an annular locating lip 11 provided on the inner surface of closure arrangement 5. End cap 9 is provided at the opposite end of body 8 and has a peripheral flange 12 which locates the cap 9 over the upper end of body 8, thereby blanking that end. End cap 9 additionally has a central well 13 which projects a short distance into the upper end of tubular body 8. Finally, end cap 9 is provided with clips 14 which serve to retain pad 11 seated in position. As shown in FIG. 1, the end cap 9 and pad 10 are sized such that there is a clearance between the peripheral edge of the pad and the interior of the housing. Thus, end cap 9, pad 10 and body 8 are spaced inwardly from cup-shaped body 3 and thereby define a flow path such that air entering at inlet A successively passes around pad 10, into the cavity between the housing 2 and the filter material 8, through filter material 8 and finally out the air outlet 6.

Tubular body 8 is preferably of a pleated material. This material is preferably silicon treated glass fibre. Pad 10 is preferably a needled synthetic material imbued with an electrical charge during the course of manufacture.

In use, the filter 1 is incorporated in the breathing circuit of a ventilator which provides nebulised drug therapy for a patient. More specifically, the filter 1 is located in the path of air exhaled from the patient and upstream of the ventilator. As such, exhaled air passes into the inlet 4 of the filter 1 as depicted by Arrow A.

The electrostatic pad 10 is in the direct path of air entering through the inlet 4 and provides a number of functions. Firstly, the electrostatic pad 10 causes air to diffuse, slow down and be diverted down between the inner surface of the housing and the outer peripheral surface of the frustoconical body 8. Secondly, the electrostatic charge on the pad 10 attracts both liquid and particles and thereby prevent their further travel through the filter. As such, the liquid and particles held in the pad 10 do not pass to the tubular filtration body 8. Thirdly, the electrostatic pad is an absorbent material and is therefore able to hold moisture. It is these second and third functions particularly that together contribute to an increase in life of the tubular filter body 8.

The filter 1 may be used in the breathing circuit until the pressure lost reaches a predetermined value, e.g. 5 millibars. At that time, the filter 1 will be removed and replaced by a new unit.

The invention is further illustrated by the following non-limiting Example.

EXAMPLE

A filter 1 as shown in the drawing was constructed in which (i) the electrostatically charged material 10 was a circular pad of TECHNOSTATIC media having a diameter of 47 mm and a thickness of 2 mm, and (ii) the tubular body 8 was a pleated HEPA filter having a height through which air could pass (i.e. excluding areas where the body was coated with glue for mounting in the filter) of 35 mm and a pleat depth of 14 mm. A similar (comparative) filter was also constructed but omitting the TECHNOSTATIC pad.

Each filter was then subjected to the following test protocol:

(i) Pressure drop (mbar) across the filter (i.e. between the inlet and outlet) was tested of air flow rates of 30, 60, 90 and 120 liters per minute. The results were recorded as "Pre-test".

(ii) The filter was placed in a humidifier at 37° C. for 24 hrs.

(iii) Pressure drop at 30, 60, 90 and 120 liters per minute was then measured. The results were recorded as "24 hr Hum".

(iv) Nebulised Ventoline was then passed to the inlet at an air flow rate of 10 liters per minute for periods of 1, 10, 10 and 10 minutes (i.e. 31 minutes total) with short intervals in between. For this procedure a total of 3 ml Ventoline was used.

(v) Pressure drop at 30, 60, 90 and 120 liters per minute were then measured and the results recorded as "31 min V".

(vi) The filter was then placed in the humidifier at 37° C. for 4 hours.

(vii) Pressure drop was then measured and recorded as "4 hr Hum".

(viii) Steps (iv)-(vii) were then repeated.

(ix) The filters were then stored overnight in plastics bags to prevent drying out.

(x) Steps (iv)-(ix) were then repeated on four successive days.

The results are shown in Table I below:

TABLE 1

| | Invention | | | | Comparative | | | |
|---|---|---|---|---|---|---|---|---|
| Day 1 | 30 L/min | 60 L/min | 90 L/min | 120 L/min | 30 L/min | 60 L/min | 90 L/min | 120 L/min |
| Pre-test | 0.61 | 1.35 | 2.05 | 3.12 | 0.69 | 1.52 | 2.38 | 3.57 |
| 24 hr Hum | 0.68 | 1.43 | 2.26 | 3.61 | 0.80 | 1.75 | 2.74 | 4.26 |
| 31 min V | 0.71 | 1.50 | 2.56 | 3.79 | 0.80 | 1.80 | 3.09 | 4.69 |
| 4 hr Hum | 0.65 | 1.44 | 2.51 | 3.69 | 0.79 | 1.75 | 2.99 | 4.46 |
| 31 min V | 0.64 | 1.47 | 2.51 | 3.64 | 0.79 | 1.72 | 3.00 | 4.60 |
| 4 hr Hum | 0.64 | 1.47 | 2.49 | 3.72 | 0.79 | 1.72 | 3.08 | 4.60 |
| Day 2 | 30 L/minin | 60 L/min | 90 L/min | 120 L/min | 30 L/min | 60 L/min | 90 L/min | 120 L/min |
| 31 min V | 0.68 | 1.49 | 2.50 | 3.68 | 0.84 | 1.90 | 3.18 | 4.82 |
| 4 hr Hum | 0.69 | 1.53 | 2.57 | 3.75 | 0.91 | 2.09 | 3.64 | 5.48 |
| 31 min V | 0.68 | 1.57 | 2.65 | 3.94 | 0.85 | 1.90 | 3.29 | 5.01 |
| 4 hr Hum | 0.75 | 1.61 | 2.71 | 4.04 | 0.97 | 2.11 | 3.66 | 5.71 |
| Day 3 | 30 L/min | 60 L/min | 90 L/min | 120 L/min | 30 L/min | 60 L/min | 90 L/min | 120 L/min |
| 31 min V | 0.72 | 1.63 | 2.78 | 4.10 | 0.99 | 2.19 | 3.85 | 5.97 |
| 4 hr Hum | 0.76 | 1.71 | 2.85 | 4.32 | 1.17 | 2.50 | 4.39 | 6.93 |
| 31 min V | 0.83 | 1.80 | 3.06 | 4.53 | 1.15 | 2.60 | 4.57 | 7.10 |
| 4 hr Hum | 0.82 | 1.78 | 2.97 | 4.56 | 1.26 | 2.88 | 5.11 | 7.83 |
| Day 4 | 30 L/min | 60 L/min | 90 L/min | 120 L/min | 30 L/min | 60 L/min | 90 L/min | 120 L/min |
| 31 min V | 0.85 | 1.95 | 3.26 | 4.89 | 1.16 | 2.71 | 4.84 | 7.41 |
| 4 hr Hum | 0.92 | 1.93 | 3.17 | 4.72 | 1.21 | 2.73 | 4.88 | 7.6 |
| 31 min V | 0.87 | 1.93 | 3.26 | 4.96 | 1.27 | 2.93 | 5.30 | 8.23 |
| 4 hr Hum | 0.69 | 1.46 | 2.48 | 3.71 | 0.90 | 1.95 | 3.37 | 5.12 |
| Day 5 | 30 L/min | 60 L/min | 90 L/min | 120 L/min | 30 L/min | 60 L/min | 90 L/min | 120 L/min |
| 31 min V | 0.69 | 1.56 | 2.64 | 3.90 | 0.93 | 2.07 | 3.64 | 5.57 |
| 4 hr Hum | 0.76 | 1.65 | 2.77 | 4.11 | 0.97 | 2.18 | 3.76 | 5.71 |
| 31 min V | 0.77 | 1.71 | 2.89 | 4.25 | 0.99 | 2.30 | 4.03 | 6.16 |
| 4 hr Hum | 0.82 | 1.77 | 2.98 | 4.43 | 1.16 | 2.44 | 4.28 | 6.63 |

The results in the above table demonstrate the superior results obtained in accordance with the invention in terms of reducing the measured pressure drop values as compared to those obtained with the Comparative filter. Attention is directed particularly to the pressure drop values obtained at the end of day 5 using an air flow rate of 120 liters per minute. The filter in accordance with the invention had a pressure drop of 4.43 mbar. In contrast the Comparative filter demonstrated a pressure drop of 6.63 mbar.

In a test protocol such as that detailed above, a pressure drop value of less than mbar (ideally less than 4.5 mbar) after 5 days testing at 120 liters per minute is the value required for a satisfactory filter.

The invention claimed is:

1. An air filter comprising;
   (i) a housing with an air inlet and an air outlet, said air outlet being provided in an end wall of the housing, and
   (ii) a filter material in the path of air flow from the inlet to the outlet, the filter material being formed as a hollow tubular body positioned coaxial with said inlet and said outlet, said tubular body having an interior cavity and being located at one of its ends on said end wall of the housing around the air outlet and being blanked at its end opposite the air outlet so that the blanked end faces the air inlet and said air flow is inwardly through the tubular body,
   (iii) an electrostatically charged material positioned at the blanked end of the tubular body and externally thereof to treat inlet air to the housing before it passes through the tubular body, the electrostatically charged material being in the form of a flat pad seated on the blanked end of the tubular body and positioned directly facing the inlet perpendicular to the direction of air flow through the inlet,
   said pad being sized such that there is a clearance between the peripheral edge of the pad and the interior of the housing whereby the pad causes incoming air to diffuse, slow down and be diverted between the interior of the housing and the exterior periphery of the tubular body so that the air may then pass through the filter material.

2. An air filter as claimed in claim 1 wherein the electrostatically charged material is retained at the blanked end of the body by means of clips.

3. An air filter as claimed in claim 1 wherein the tubular body is frustoconical and tapers from the air outlet towards the air inlet.

4. An air filter as claimed in claim 1 wherein the filter material is pleated.

5. An air filter as claimed in claim 1 wherein the filter material is a silicone treated glass fibre.

6. An air filter as claimed in claim 1 wherein the electrostatically charged material is a fibrous material.

7. An air filter as claimed in claim 1 wherein the electrostatically charged material is a needled synthetic material imbued with an electrical charge during the course of manufacture.

8. An air filter as claimed in claim 1 wherein the filter material is a HEPA filter.

9. A ventilator assembly having a breathing circuit incorporating an air filter as claimed in claim 1.

10. An air filter as claimed in claim 1 wherein the electrostatically charged material is of larger cross-sectional size than the air inlet.

11. An air filter comprising;
    (i) a housing with an air inlet and an air outlet, said air outlet being provided in an end wall of the housing, and
    (ii) a filter material in the path of air flow from the inlet to the outlet, the filter material being formed as a hollow tubular body positioned coaxial with said inlet and said outlet, said tubular body having an interior cavity and being located at one of its ends on said end wall of the housing around the air outlet and being blanked at its end opposite the air outlet so that the blanked end faces the air inlet and said air flow is inwardly through the tubular body, and
    (iii) an electrostatically charged material positioned at the blanked end of the tubular body and externally thereof to treat inlet air to the housing before it passes through the tubular body, the electrostatically charged material being in the form of a flat pad seated on the blanked end of the tubular body and positioned directly facing the inlet perpendicular to the direction of air flow through the inlet,
    the electrostatically charged material and the filter material being spaced inwardly from the housing and defining a flow path such that air entering the air inlet successively passes around the electrostatically charged material, between the filter material and the housing, through the filter material, and out the air outlet,
    whereby the pad causes incoming air to diffuse, slow down and be diverted between the interior of the housing and the exterior periphery of the tubular body so that the air passes through the filter material.

12. The air filter of claim 11 and which further includes an end cap attached to the hollow tubular body at the end opposite the air outlet, and the electrostatically charged material is mounted adjacent the end cap and facing the inlet.

* * * * *